United States Patent [19]

Falkowski et al.

[11] 4,365,058

[45] Dec. 21, 1982

[54] METHOD OF PREPARATION OF ESTERS OF ANTIBIOTICS SELECTED FROM THE GROUP CONSISTING OF POLYENE MACROLIDES AND OF N-SUBSTITUTED DERIVATIVES THEREOF

[75] Inventors: Leonard S. Falkowski, Gdańsk; Barbara J. Stefanska; Elżbieta Troka, both of Gdansk-Oliwa; Jerzy J. Golik, Sopot; Edward Borowski, Gdańsk-Wrzeszcz, all of Poland

[73] Assignee: Politechnika Gdańska, Gdansk, Poland

[21] Appl. No.: 166,598

[22] Filed: Jul. 7, 1980

[30] Foreign Application Priority Data

Jul. 18, 1979 [PL] Poland .................................. 217239

[51] Int. Cl.[3] ............................................ C07H 17/08

[52] U.S. Cl. ...................................... 536/6.5; 536/119

[58] Field of Search ................... 536/17 C, 17 R, 115, 536/119

[56] References Cited

U.S. PATENT DOCUMENTS

| | | | |
|---|---|---|---|
| 2,628,249 | 2/1953 | Bruno et al. | 536/119 |
| 3,780,173 | 12/1973 | Bruzzese et al. | 424/122 |
| 4,035,568 | 7/1977 | Schaffner et al. | 536/17 C |

*Primary Examiner*—Johnnie R. Brown

[57] ABSTRACT

A process for production of esters of antibiotics from the group of polyene macrolides and of N-substituted derivatives thereof, having the general Formula 1, wherein R denotes the radical of antibiotic or of its R-COOR, I N-substituted derivative, and $R_1$ denotes an alkyl with the chain length of $C_1$ through $C_5$, or an aryl, consisting therein that an antibiotic from the group of polyene macrolides or its N-substituted derivative is dissolved or suspended in alcohol and/or neutral organic solvent, or in a mixture of organic solvents, in presence of dicyclohexylcarbodiimide and/or hydrocybenzotriazole, the whole is allowed to stand at room temperature, or at temperature elevated to 40° C., and then the obtained product is isolated from the reaction medium after known methods.

3 Claims, No Drawings

METHOD OF PREPARATION OF ESTERS OF ANTIBIOTICS SELECTED FROM THE GROUP CONSISTING OF POLYENE MACROLIDES AND OF N-SUBSTITUTED DERIVATIVES THEREOF

This invention relates to a process for production of esters of antibiotics from the group of polyene macrolides and of N-substituted derivatives thereof, of the formula of the drawing (hereinafter Formula I), wherein R denotes the radical of antibiotic or of its N-substituted derivative, and $R_1$ denotes an alkyl with the chain length of one to five carbon atoms, or an aryl group.

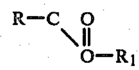

I

Alkyl esters of polyene macrolides, known from the U.S. Pat. No. 3,780,173 and from the publication of T. Bruzzesse et al., J. Pharmaceut. Sc., 64, 462, 1965, as amphotericin B, nystatin, partricin, show an antimycotic activity of the same order as the crude antibiotics, and toxicity lower than that thereof, and with acids they form salts well dispersable in water.

Extensive studies have been carried out on methyl ester of amphotericin B—D. P. Boner et al., J. Antibiot., 28, 132, 1975, and D. P. Boner et al., Antimicrob. Agents Chemotherap., 7, 724, 1975.

Process for production of alkyl esters of antibiotics from the group of polyene macrolides, is know from the U.S. Pat. No. 4,035,568 consists in reacting the antibiotic in form of a suspension or solution in an organic solvent with diazoalkanes.

There are also known methyl esters of N-substituted derivatives of antibiotics from the group of polyene macrolides, from the Polish Patent Application No. 212007, which are obtained in the reaction of N-substituted derivative of macrolide, in form of a solution in an organic solvent, with dimethyl sulfate in presence of a neutralizing agent, whereafter methyl ester of N-substituted polyene macrolide is isolated, or contingently the substituent on amino group is removed.

An inconvenience of the process according to the U.S. Pat. No. 4,035,568 is that the explosive and toxic properties of diazoalkanes make the working therewith hazardous, especially on industrial scale. This complicates in an essential way the technique of production of said compounds, being additionally made difficult by generation of disadvantageous by-products.

An inconvenience of its process according to the Polish Patent Application is the restriction only to the synthesis of methyl esters of polyene macrolides and N-substituted derivatives thereof, and the necessity of additional operations of removal for the amino group substituent in case of synthesis of methyl esters of antibiotics from the group of polyene macrolides.

THE INVENTION

The process for production of esters of antibiotics from the group of polyene macrolides and its N-substituted derivatives, having the general Formula I:

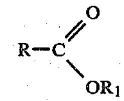

I wherein R denotes the antibiotic radical of antibiotic or its N-substituted derivative, and $R_1$ is an alkyl having the chain length of one to five carbon atoms, or an aryl, according to this invention, consists therein that the antibiotic from the group of polyene macrolides or its N-substituted derivative is dissolved or suspended in alcohol and/or a neutral organic solvent or in a mixture of neutral organic solvents, in presence of dicyclohexylcarbodiimide and/or hydroxybenzotriazole, the composite being allowed to react at from room temperature up to about 40° C., whereafter the obtained product is isolated from the reaction medium by known methods.

As the antibiotic from the group of polyene macrolides there are employed: pimaricin, rimocidin, nystatin, polyfungin, amphotericin B, candicidin, levorin, aureofacin.

As N-substituted derivatives there are employed acetyl-substituted polyene macrolides, or polyene macrolides substituted with N-($N^1$,$N^1$-dimethylamino)-methylene, so called BMAM-derivatives, with N-penten-2-on-3-yl-2, so called NPA-derivatives, and with N-(1-carboalkoxy)-propen-1-yl-2, so called NPO-derivatives.

As the alcohol entering into reaction with the carboxyl group of the antibiotic, aliphatic or aromatic alcohols are used, accordingly to the ester desired.

As neutral organic solvents N,N-dimethylacetamide, N,N-dimethylformamide, pyridine, and tetrahydrofuran are employed.

The structure of obtained derivatives was verified by comparison with the crude antibiotic from the group of polyene macrolides, and by means of the spectroscopic analysis in ultraviolet, visible, and in infra-red light, and mass spectrometry carried out in field desorption procedures. The absorption spectra within the visible light and ultraviolet light of obtained esters and of the crude antibiotics differ only insignificantly in their intensity, the maximum absorption positions and the oscillation structure being identical. That proves an unchanged structure of polyene chromophore in the obtained derivatives.

Evidence of presence of the ester bond in the molecule of the abtibiotic derivative is the occurrence of an intensive absorption band in infra-red spectrum at $\nu=1730$ $cm^{-1}$ /for aliphatic and aromatic esters/ with simultaneous absence for the band of carboxylate ion, being characteristic for the crude antibiotic at $\nu=1590$ $cm^{-1}$.

An advantage of the process is the possibility of obtaining of various types of aliphatic and aromatic esters of polyene macrolides.

The process for production of esters of antibiotics from the group of polyene macrolides and their N-substituted derivative, according to the invention, will be now illustrated by means of the following examples.

EXAMPLE I 1 g of nystatin /$E_{1\ cm}^{1\%}=800$ at 304 nm/, 1 g of dicyclohexylcarbodiimide /hereinafter called DCCJ/ are dissolved in 200 $cm^3$ of anhydrous methanol and agitated at the temperature of 40° C. for 15 hours.

Within this time practically the whole of antibiotic is reacted. The course of the reaction is controlled by means of thin-layer chromatography in the system of ethyl acetate:acetic acid:water /4:1:1/. Then methanol is evaporated under reduced pressure to a volume of a few $cm^3$ and the antibiotic precipitated with ethyl ether. After purification the product is centrifuged, washed in turns with ethyl ether and hexane and dried under reduce pressure. There are obtained 0.9 g of raw nystatin methyl ester with $E_{1\,cm}^{1\%}=650$ at 304 nm.

After purification using the method of column chromatography on Sephadex LH 20 in the system of chloroform:methanol /5:1/ 0.8 g of nystatinmethyl ester /$E_{1\,cm}^{1\%}=720$ at 304 nm/ are obtained that constitutes 60% of theoretical yield.

EXAMPLE II

To 1 g of nystatin ($E_{1\,cm}^{1\%}=800$ at 304 nm) and 1 g of DCCJ 20 ml of freshly distilled benzyl alcohol are added, the whole being agitated until dissolved and allowed to stand over night. The product is precipitated with an addition of 1300 ml of mixture of ethyl ether with hexane (2:1), centrifuged, washed in turns with ethyl ether and hexane, and dried under reduced pressure. There are obtained 0.75 g of crude product with $E_{1\,cm}^{1\%}=670$ at 304 nm, being then purified after column chromatography method on Sephadex LH 20 in the system of chloroform:methanol (10:1). There are obtained 0.65 g of nystatin benzyl ester with $E_{1\,cm}^{1\%}=760$ at 304 nm, that constitutes 60% of theoretical yield.

EXAMPLE III 0.4 g of nystatin, 0.3 g of DCCJ, and 0.5 g of p-nitrophenol are dissolved in a mixture of 3 $cm^3$ of N,N-dimethylacetamide and pyridine (1:1) and allowed to stand for night at the temperature of 40° C. After precipitation with ethyl ether and multiple washing with ether and hexane, 0.35 g of crude product ($E_{1\,cm}^{1\%}=630$ at 304 nm) are obtained. This is purified by the column chromatography method on silica gel saturated preliminarily with water, in the system of Chloroform:butanol:water (20:20:1), and 0.3 g of nystatin p-nitrophenyl ester ($E_{1\,cm}^{1\%}=680$ at 304 nm) is obtained, that constitutes 65% of theoretical yield.

EXAMPLE IV 0.5 g of nystatin and 0.5 g of DCCJ are dissolved in 3 $cm^3$ of saturated solution of phenol in N,N-dimethylacetamide and allowed to stand over night at the temperature of 40° C. The product is precipitated with ethyl ether, and purified using column chromatography method on silica gel saturated preliminarily with water, in the system of chloroform:methanol:water /20:10:0.5/. There are obtained 0.3 g of nystatin phenyl ester /$E_{1\,cm}^{1\%}=700$ at 304 nm/, that constitutes 55% of theoretical yield.

EXAMPLE V 1 g of NPA-derivative of aureofacin with $E_{1\,cm}^{1\%}=700$ at 378 nm and 0.5 g of DDCJ are dissolved in 20 $cm^3$ of mixture of methanol and tetrahydrofuran /1:1/ and allowed to stand over night at the temperature of 40° C. Then the whole is concentrated under reduced pressure to several $cm^3$, and the product is precipitated with ethyl ether. There are obtained 0.9 g of methyl ester of NPA-derivative of aureofacin /$E_{1\,cm}^{1\%}=500$ at 378 nm/.

EXAMPLE VI 0.5 g of NPA-derivative of candicidin /$E_{1\,cm}^{1\%}=500$ at 383 nm/ and 0.4 g DCCJ are dissolved in 10 $cm^3$ of a mixture of methanol and tetrahydrofuran /1:1/ and allowed to stand over night at the temperature of 40° C. Isolation as per Example V. There are obtained 0.45 g /$E_{1\,cm}^{1\%}=400$/ that constitutes 80% of theoretical yield.

EXAMPLE VII 0.3 g of N-acetopimaricin with $E_{1\,cm}^{1\%}=110$ at 304 nm and 0.2 g of DCCJ are dissolved in 2 ml of freshly distilled benzyl alcohol and allowed to stand over night at room temperature. The residue precipitated with a mixture of ethyl ether:hexane (2:1) is supplied to the column filled with the gel Sephadex LH 20 and submitted to chromatography in the system of chloroform:methanol (5:1). There are obtained 0.2 g of N-acetopimaricin benzyl ester ($E_{1\,cm}^{1\%}=1000$ at 1304 nm), that constitutes 60% of theoretical yield.

EXAMPLE VIII 0.5 g of N-acetoamphotericin B with $E_{1\,cm}^{1\%}=1200$ at 383 nm and 0.4 g of DCCJ are dissolved in 5 ml of freshly distilled benzyl alcohol and allowed to stand over night at room temperature. The procedure of isolation as per Example VII. There are obtained 0.45 g of N-acetoamphotericin B benzyl ester with $E_{1\,cm}^{1\%}=1200$ at 383 nm, that constitutes 85% of theoretical yield.

EXAMPLE IX 0.5 g of N-acetylnystatin ($E_{1\,cm}^{1\%}=900$ at 304 nm) and 0.4 g of DCCJ are dissolved in 13 ml of freshly distilled benzyl alcohol and allowed to stand over night at room temperature. The procedure of isolation as per Example VII. There are obtained 0.4 g of N-acetylnystatin benzyl ester ($E_{1\,cm}^{1\%}=780$ at 304 nm), that constitutes 75% of theoretical yield.

EXAMPLE X 1 g of polyfungin ($E_{1\,cm}^{1\%}=650$ at 304 nm) are dissolved in 10 ml of anhydrous methanol, thereafter 1 g of dicyclohexylcarbodiimide is added and the whole is agitated for 24 hours at room temperature. The progress of reaction is controlled by means of thin-layer chromatography in the system of ethyl acetate:acetic acid:water (4:1:1). Then 5 ml of butanol are added, methanol is evaporated under reduced pressure, whereafter it is, by means of ethyl ether, precipitated the residue of polyfungin methyl ester. The precipitated product is washed about 3 times and dried under reduced pressure. There are obtained 580 g of polyfungin methyl ester with $E_{1\,cm}^{1\%}=760$ at 304 nm, that constitutes about 70% of theoretical yield. $IC_{50}=0.25$ mcg/ml.

EXAMPLE XI 0.5 g of NPA-derivative of amphotericin B with $E_{1\,cm}^{1\%}=1550$ at 382 nm are dissolved in 5 ml of anhydrous ethanol, then 0.5 g of DCCJ are added and the mixture is agitated at room temperature for 24 hours. The reaction is controlled by means of the thin-layer chromatography in the system of ethyl acetate:acetic acid: water (4:1:1). Then 1 ml of pyridine is added, and after 4 hours from the solution the residue of ethyl ester of NPA-derivative of amphotericin B is precipitated. The residue is washed two times with ethyl ether and dried under reduced pressure. There are obtained 0.4 g of ethyl ester of NPA-derivative of amphotericin B, $IC_{50}=0.05$ mcg/ml, that constitutes about 80% of theoretical yield ($E_{1\ cm}^{1\%}=1260$ at 382 nm.

The residue of the ethyl ester of NPA-derivative of amphotericin B is dissolved in a system of Chloroform:methanol:water (100:10:1) and supplied to a column of Sephadex LH 20. After the column 250 mg of ester with $E_{1\ cm}^{1\%}=1400$ are isolated.

EXAMPLE XII 0.5 g of NPA-derivative of nystatin with $E_{1\ cm}^{1\%}=850$ are dissolved in 100 ml of ethanol, 0.4 g of DCCJ are added and the whole is allows to stand for 24 hours at room temperature. The obtained product, ethyl ester of NPA-derivative of nystatin is precipitated with ethyl ether, washed two times with ethyl ether and dried under reduced pressure. There are obtained 0.5 g of ethyl ester of NPA-derivative of nystatin with $E_{1\ cm}^{1\%}=500$, and with $IC_{50}=0.5$ mcg/ml.

EXAMPLE XIII 100 mg of NPA-derivative of amphotericin with $E_{1\ cm}^{1\%}=1560$ at 382 nm are dissolved in 20 ml of butanol, then 100 mg of DCCJ are added and the whole is allowed to stand for 24 hours at the temperature of 36° C. After proving the completeness of the reaction by means of thin-layer chromatography in a system of ethyl acetate:acetic acid:water (4:1:1), from the reaction mixture the residue is precipitated with ethyl ether, which is washed two times with ethyl ether and dried under reduced pressure. There are obtained 85 g of butyl ester of NPA-derivative of amphotericin B with $E_{1\ cm}^{1\%}=1000$, that constitutes 80% of theoretical yield.

EXAMPLE XIV 0.4 g of NPA-derivative of pimaricin with $E_{1\ cm}^{1\%}=900$ at 304 nm are dissolved in 20 ml of anhydrous methanol and 100 mg of DCCJ are added. After 20 hours of reaction at the room temperature its course is tested after the thin-layer chromatography method /practically the entire NPA-derivative is reacted/. The residue is precipitated with ethyl ether from methanol, and is two times washed with ethyl ether and dried under reduced pressure. There are obtained 14 mg of methyl ester of NPA-derivative of pimaricin with $E_{1\ cm}^{1\%}=600$. $IC_{50}=4$ mcg/ml.

EXAMPLE XV 50 mg of candicidin with $E_{1\ cm}^{1\%}=600$ is dissolved in 1 ml of pyridine, and 50 mg of dicyclohexylcarbodiimide and 50 mg of hydroxybenzotriazole are added. After 1 hour agitation at the temperature of 40° C. 3 ml of methanol are added and allowed to stand for 24 hours at room temperature. The reaction product is precipitated with ethyl ether, then it is washed two times with ethyl ether and dried under reduced pressure. There are obtained 35 mg of methyl ester of candicidin with $E_{1\ cm}^{1\%}=550$. $IC_{50}=0.001$ mcg/ml.

EXAMPLE XVI

To 50 mg of polyfungin with $E_{1\ cm}^{1\%}=650$ there are added 1 ml of anisic alcohol and 50 mg of DCCJ are added. The reaction is conducted for 10 hours at the temperature of 40° C. The course of the reaction is controlled after the thin-layer chromatography method in the system of chloroform:methanol:water /100:25:3/. On completing the reaction the product is precipitated with ethyl ether, washed two times with ethyl ether, and dried under reduced pressure. There are obtained 30 mg of polyfungin anisic ester with $E_{1\ cm}^{1\%}=650$. $IC_{50}=0.4$ mcg/ml. Yield 65%.

What is claimed is:

1. A method of esterifying polyene microlide antibiotics having a carboxyl group and selected from the group consisting of nystatin, aureofacin, candicidin, pimaricin, amphotericin B and polyfungin and the N-substituted acetyl and N-penten-2-on-3-yl-2 derivatives of these antibiotics, which comprises the steps of reacting said antibiotic compound with an alcohol selected from the group consisting of one to five carbon aliphatic alcohols and monocyclic aryl alcohols; in at least one neutral organic solvent therefor; in the presence of a reaction promotor selected from the group consisting of dicyclohexyl carbodiimide and mixtures of dicyclohexyl carbodiimide with hydroxybenzatriazole; at temperatures up to 40° C. until completion, isolating said ester and then purifying same.

2. The method according to claim 1, wherein the aliphatic alcohol is selected from the group consisting of: methanol, ethanol, butanol, and the aryl alcohols-phenol, p-nitrophenol, benzyl and anisic alcohols.

3. The method according to claim 1, wherein said neutral organic solvent is selected from the group consisting of N,N-dimethylacetamide, pyridine and tetrahydrofuran and mixtures thereof.

* * * * *